United States Patent [19]

Friswell

[11] 4,094,196

[45] June 13, 1978

[54] SAMPLE INJECTION WITH AUTOMATIC CLEANING OF SAMPLING CONDUIT

[75] Inventor: David R. Friswell, Holliston, Mass.

[73] Assignee: Waters Associates, Inc., Milford, Mass.

[21] Appl. No.: 772,145

[22] Filed: Feb. 25, 1977

[51] Int. Cl.² .............................................. G01N 1/14
[52] U.S. Cl. ................................................ 73/422 GC
[58] Field of Search ......... 23/259; 73/423 A, 422 GC

[56] References Cited

U.S. PATENT DOCUMENTS

| | | | |
|---|---|---|---|
| 3,552,212 | 1/1971 | Ohlin | 73/423 A |
| 3,824,859 | 7/1974 | Harris et al. | 73/422 GC |
| 3,848,469 | 11/1974 | Chizhov | 73/422 GC |
| 3,916,692 | 11/1975 | Abrahams | 73/422 GC |

*Primary Examiner*—S. Clement Swisher
*Attorney, Agent, or Firm*—Irons and Sears

[57] ABSTRACT

An automatic liquid sample-injecting apparatus using a conduit such as a hypodermic needle or pipette to suck liquid from a sample source and transfer it to an injector valve apparatus. The apparatus utilizes the optimum embodiment of the apparatus being equipped with (1) novel seal means adapted to exert a radial thrust or wiping action on the conduit and (2) novel conduit working means featuring both a drip-proof means to supply a non-contaminating solvent for washing the exterior of the needle and means to remove such solvent, all without interfering with the use of the needle in a series of automatic injections.

14 Claims, 6 Drawing Figures

SAMPLE INJECTION WITH AUTOMATIC CLEANING OF SAMPLING CONDUIT

BACKGROUND OF THE INVENTION

In liquid chromatography it has been a problem to provide means to inject discrete liquid samples into a liquid chromatograph column with a minimum of dilution of "peak-spreading" as it is called in the chromatographic art. Applicant set out to provide an apparatus useful in the injection to an l.c. column sequence of a large number of liquid samples. Such sequential testing apparatus is known to be useful in such testing procedures as quality control testing in the pharmaceutical industry and the like.

In general, the schematic injection scheme selected by the Applicant is that disclosed in U.S. Pat. No. 3,916,692 to Abrahams. Applicant, in adapting that scheme to a reciprocating sampling conduit adapted to enter a series of sample containers encountered a number of design problems, the most critical of which was the sealing of the outlet of the reciprocating sample conduit into the liquid chromatographic flow circuit. It is to be understood that in the chromatographic processes being discussed, fluids are handled at pressures of 5000 psig and even higher.

As will be described below, the particular apparatus constructed to meet the various problems meets, and even surpasses, the prior standard of performance established by the apparatus described in U.S. Pat. No. 3,916,692.

In liquid chromatography and numerous other analytical procedures in the chemical and medical arts, it is desirable to have a large number of samples handled sequentially on the same apparatus. In such cases, a conduit, often a hypodermic needle or the like, is dipped into a series of different samples. In such situations, there is an increased danger of cross-sample contamination because of sample from an earlier operation being dipped into a second operation.

It has been a problem in the art to provide a dripproof, conduit-cleaning procedure which can be rapidly used without slowing the sample feeding procedure. As will be described below, Applicant has, for the first time, achieved such a drip proof, contamination avoiding, conduit cleaning means. This apparatus is particularly valuable in conjunction with automatic liquid sampling apparatus in liquid chromatography.

SUMMARY OF THE INVENTION

Therefore, it is a principal object of the invention to provide an improved injector valve mechanism for use in feeding of discrete samples of liquid to analytical apparatus, especially to liquid chromatographic apparatus. It is a particular object of the invention to provide such apparatus adapted for automatic operation.

Another object of the invention is to provide a liquid sample injector and valve mechanism of the type which is provided with a self-cleaning sample conduit.

Still another object of the invention is to provide liquid sampling apparatus which comprises an automatically cleaned, non-drip reciprocating sample needle and means to discharge the needle directly into a sample loop without any substantial leakage of the sample around the conduit even at pressures of the order of 5000 psig.

Another object of the invention is to provide a novel seal means to facilitate the sealing of the opening of the reciprocating conduit within the injector-sample flow circuit.

Further objects of the invention include providing the individual novel and improved seal means and wash means described above and also providing the novel processes by which all of the above-mentioned injector valves, washing means, and seal means are operated and constructed.

Other objects of the invention will be obvious to those skilled in the art on their reading of this invention.

Moreover, it should be noted that, in the achievement of the aforesaid objects, an injector was constructed which actually outperforms the best previous injectors in terms of the precision with which samples are discharged from the injector into a liquid chromatograph or other analytical devices. In chromatography, this precision results in sharper resolution of peaks representing various chemical compounds.

The above objects have been substantially achieved, with respect to the injector valve, by the construction of a novel apparatus.

ILLUSTRATIVE EMBODIMENTS OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

Figure 1:
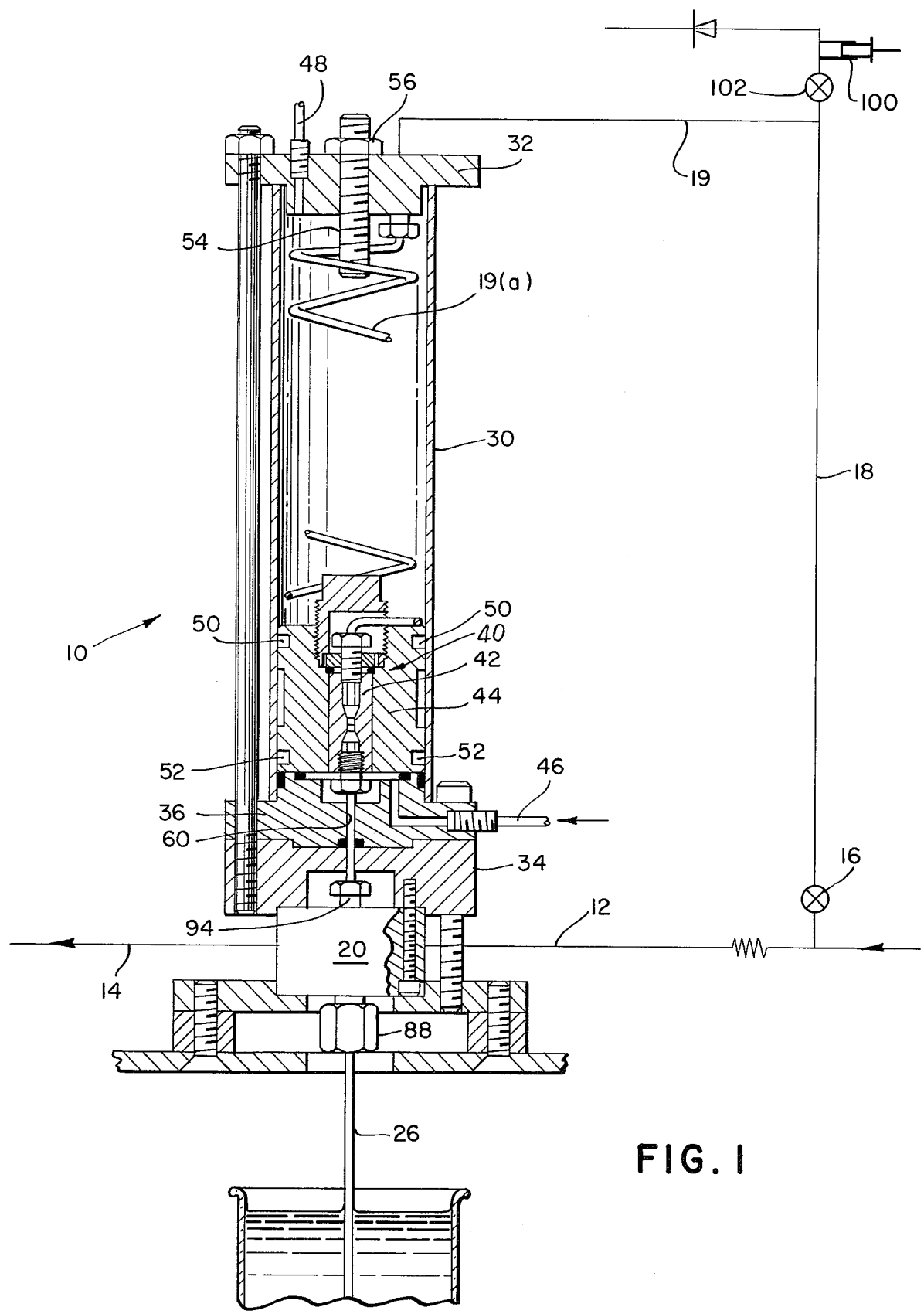
FIG. 1 is a novel injector valve assembly constructed to facilitate automatic sample injection.

Referring now to FIG. 1, it is seen that injector valve assembly 10 comprises a number of connections to various conduits as is generally known in the liquid chromatographic art. Thus, conduit 12 runs from a pump (not shown) supplying a carrier solvent into the injector valve assembly 10 and, in a first mode of operation, communicates with an outlet conduit 14 and proceeds into a chromatographic column (not shown). To do this, the liquid must proceed through needle-valving block 20, best seen in FIG. 2. Block 20 comprises an inlet port 22 and an outlet port 24 communicating with conduits 12 and 14, respectively. A sampling conduit means, a modified hypodermic needle 26 is adapted for reciprocating vertical movement in block 20. When the needle is in its lowered position, there is an annular space 26(a) about the needle around which fluid can flow from conduit 22 to 24. When the needle is raised the lower portion thereof, i.e. portion 27, is a plug means which effectively seals the fluid with lower seal 70.

In the first mode of operations, a valve 16 in conduit 18 is closed. When valve 16 is opened to establish the sample injection mode, most liquid from the pump will leave conduit 12 and flow through conduit 18, and conduit 19, into extensible tubing 19(a) and thence to needle 26, to port 24, conduit 14 and to the chromatographic column.

Figure 6:
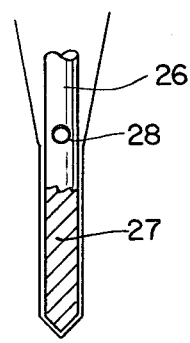
FIG. 6 illustrates a sampling conduit useful with the present invention.

FIG. 6 shows needle 26 with its outlet port 28 preferably in register with the port 24. The bottom portion 27 of the needle is solid and forms no part of the needle conduit.

Referring again to FIG. 1, it is seen that the connection means 40 of needle 26 to conduit 19(a) is formed within a steel insert block 42 which, in turn, is carried in an aluminum piston 44. Piston 44 is air operated. The piston 44 moves in a cylindrical housing 30 having a top housing plate 32 and lower housing plates 34 and 36. The lower plates 34 and 36 have a central channel 60 which also continues into block 20 and in which sampling conduit 26 reciprocates. Air to raise the piston 44 (and, of course, needle 26 connected thereto) enters conduit 46; air to lower the piston enters conduit 48. These air connections are connected to a pneumatic control system which is not shown because it forms no part of the invention as claimed herein and because those skilled in the art can readily manufacture and adapt such systems to meet their particular requirements. The piston is provided with lip seals at 50 and 52. Travel of the piston can be adjusted by modifying the vertical position of a stop bar 54 with positioning nut 56. As indicated above, the ideal position is such that port 28 from needle 26 is in register with port 24.

Connection 40 comprises ferrules on each of needle 26 and conduit tubing 19(a). These form a butt connection utilizing fittings already well known in the chromatography art.

FIGS. 2 through 5 all illustrate an important sealing structure on which the combination of simplicity and high-pressure capability of the invention depends. At positions just above and below that point in needle channel 60 to which conduit 28 can be raised in order to communicate with port 24 it is necessary to have an efficacious seal means that will be able to handle pressures to 5000 – 6000 psig, will be able to do so without binding of the needle 26, and will be able to do so for a prolonged period of time without replacement. In this connection, it should be understood that the apparatus of the invention is intended to be utilized in analytical work wherein it handles, routinely, samples as small as 5 microliters or smaller. Moreover, it must be realized that the chemical sensitivity of the analytical process being used is such that most organic materials of construction cannot be utilized because of chemical contaminants which would be leached therefrom. Thus the problem faced by the Inventor combined a rare combination of hydraulic, chemical and mechanical restraints. Nevertheless, the problem has been successfully solved by utilization of combination of seals 70 comprising a sleeve 72 formed of a fluorocarbon-based material. It is desirable that the fluorocarbon be reinforced; otherwise shredding or peeling of the seal may result. Advantageously, the material will have tensile and compressive strengths exceeding 1600 and 1200 psi respectively. A suitable material is well known in the art and sold under the trade designation RULON J by Dixon Corporation. Stress rings 74 may be separate pieces as illustrated for the highest and lowest rings of FIG. 2 herein or may be made integral with block 20 for the intermediate rings. Indeed, in the case of the rings nearer the ports 22 and 24, it is desirable to fabricate the stressing rings into block 20.

Figure 3:
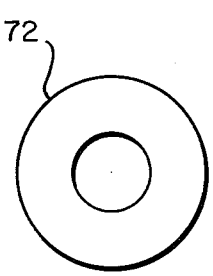
FIG. 3 is a plan view of the resin part of a wiper seal shown in FIG. 2.

FIG. 3 shows the sleeve 72 of seal 70. It has an outside diameter of 0.152 inches and an inside diameter of 0.059 inches (when used with a needle of a 0.057 inch outside diameter). These diameters are concentric within 0.003 inches. It is to be noted that the sleeve does not comprise any indentation as it is fabricated. In the illustrated embodiment of the invention, sleeve 72 is 0.120 inches long and is formed of a resin (as opposed to glass or asbestos) reinforced. This material has superior functional characteristics when compared to most reinforced halogenated polymer resins. It is also characterized by a minimum tensile strength of 2000 psi and a compressive strength of about 1430 psi.

Figure 4:
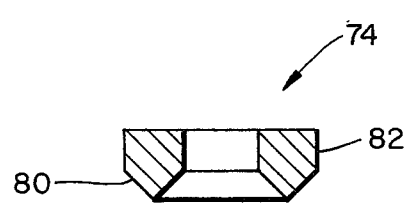
FIG. 4 is a section of the stressing insert used with, and forming part of the seal shown in FIG. 3.

FIG. 4 illustrates the stressing ring. In the illustrated embodiment of the invention, it comprises a sleeve-deforming surface 80 bevelled to a 90° angle, has a bore of 0.0165 inch diameter, and an outside diameter of 0.151 inches. The flat side wall 82 is 0.05 inches long.

Figure 5:
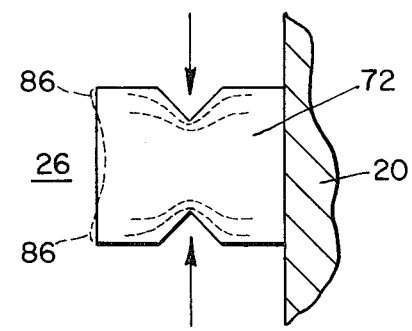
FIG. 5 is a schematic explanation of the function of wiper-seals shown in FIG. 3.

FIG. 5 is a highly schematic diagram of a portion of sleeve 72 of seal 70 showing how strain applied to sleeve 72 through rings 74 cause the seal to push out at 86 tending to seal against needle 26. As will be seen in FIG. 2, this pressure is achieved as the result of compression between washer housing 88 wherein an extension 90 is threaded into block 20 to bear on the bottom most seal ring 74 which, in turn, pushes the lower seal 70 against a portion 92 of block 20. Similarly, the uppermost of seals 70 is compressed downwardly by a positioning sleeve 94 which, like extension 90 is arranged concentrically with needle 26.

It is to be noted that in normal liquid chromatographic procedures, there is usually no problem in cleaning the interior conduit sampling needle 26. After a sample has been sucked into needle 26 by a suction syringe 100, and the needle has been pneumatically raised to its proper discharge point, i.e. with orifice 28 facing outlet conduit 24; then valve 102 is closed, valve 16 is opened and most solvent flow goes through conduits 18 and 19, 19(a), etc. This flow not only sweeps the sample into chromatographic column but it also continues for a sufficient time thereafter to assure that no substantial sample contamination remains in the needle. Such a delay is normally inherent in the nature of column chromatography.

Figure 2:
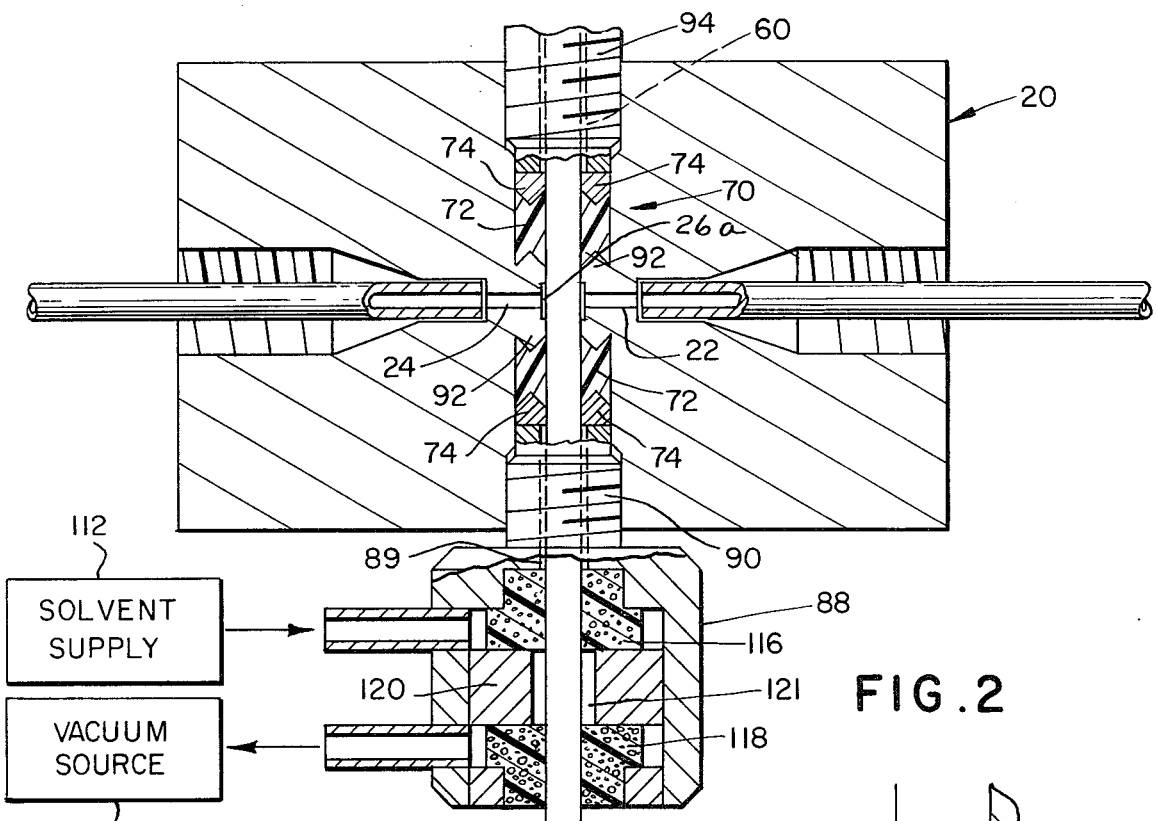
FIG. 2 is a detailed elevation, partly in section, of that portion of the injector valve at which (a) the sampling conduit is jointed to the fluid flow pattern of the rest of the injector and (b) the sampling conduit is automatically washed.

As illustrated in FIG. 2, Applicant has undertaken to provide a novel, dripless, sample-conduit washing means 110.

Washer 110 comprises a solvent supply reservoir 112 and a vacuum source 114, both shown schematically on FIG. 2. Within washer housing 88, is a bore 89 through which needle 28 moves vertically during operation of the sample injector. About bore 89 are mounted two highly porous plugs 116 and 118 of a sintered material, e.g. polypropylene, polytetrafluoroethylene, or the like. The plugs have pores of about 20 to 40 microns in size. These are separated by a spacer member 120. They are snug against the needle, but without constricting its vertical movement. Although the operation of the washer may be timed manually, it is desirable that it be automated to (1) supply solvent to plug 116 when the needle is down and (2) apply a vacuum to plug 118 when the needle is up.

Washer 10, therefore, provides means via plug 116 to wet the needle while it is depressed and wipe the needle with solvent as the needle rises. Any excess solvent flows through the annular space 121 between spaces 116 and 118 and is distributed within lower plug 118 and carried away in an air stream pulled upwardly through plug 118 and towards vacuum source 114. This procedure avoids any dripping of solvent from the washer. Plug 118 also forms means to wipe the needle as it moves upwardly out of the sample bottle.

It will be apparent to those skilled in the art that the drawings are schematic. For example, the conduits used in liquid chromatography are generally smaller than those shown. Moreover, to simplify the drawings, the fittings have been omitted as at ports 22 and 24. However, such fittings are well known in the art and form no inventive aspect of the present disclosure.

There is substantial advantage in having the orifice 28 of needle 26 directly face port 24. However, such relative placement of orifice and port substantially reduce the risk of a premature loss of meniscus liquid from the face of the orifice before the intentional sample outflow from the sampling conduit.

It is also to be understood that the following claims are intended to cover all of the generic and specific features of the invention herein described and all statements of the scope of the invention which might be said to fall therebetween.

What is claimed is:

1. In a liquid sample injection apparatus of the type comprising a sample loop, means to supply discrete samples to said loop from a first end thereof and means to supply solvent from the second end thereof to push said sample out of said injection apparatus at an injector outlet port, and wherein said apparatus also comprises means to continuously supply solvent through a conduit by-passing said sample loop and thence to said injector outlet port at the same site at which said sample loop is emptied into said outlet port, the improvement
    wherein said means to supply discrete samples to said loop comprises a sampling conduit that forms part of said sample loop and is moveable in a vertical channel between a sample-intake position and a sample-discharge position,
    wherein said sampling conduit comprises a discharge orifice on one side thereof which, in the sample-discharge position, is adapted to discharge fluid into said outlet port
    wherein said sampling conduit comprises a plug member below said discharge orifice to seal said channel when said sampling conduit is in the raised position, and
    wherein said means to supply solvent through a conduit bypassing said sample loop includes an annular passage proximate said orifice when said orifice is in its sample-discharge position.

2. In a liquid sample injection apparatus of the type comprising a sample loop, means to supply discrete samples to said loop from a first end thereof and means to supply solvent from the second end thereof to push said sample out of said injection apparatus at an injector outlet port, and wherein said apparatus also comprises means to continuously supply solvent through a conduit by-passing said sample loop and thence to said injector outlet port at the same site at which said sample loop is emptied into said outlet port, the improvement wherein:
    said means to supply discrete samples to said loop comprises a sampling conduit that forms part of said sample loop and is movable in a vertical channel between a sample-intake position and a sample-discharge position,
    wherein said sampling conduit comprises a discharge orifice on one side thereof which, in the sample-discharge position, is adapted to discharge fluid into said outlet port and
    wherein said sampling conduit comprises a plug member below said discharge orifice to seal said channel when said sampling conduit is in the raised position,
    said apparatus further comprising, a means to wash the exterior of said sample conduit, said washing means comprising:
        (a) a housing in which said sampling conduit moves up and down, said housing comprises porous wiping means in snug contact with said needle;
        (b) means to distribute a supply of wash liquid to said needle through said porous wiping means;
        (c) means to move air through said porous wiping means at a position below said wash-liquid supply means; and
        (d) means to remove said air from said washing means at a position below said wash-liquid supply means.

3. Apparatus as defined in claim 2 wherein said porous wiping means is a sintered material having a pore size of from about 20 to 40 microns.

4. Apparatus as defined in claim 2 wherein said porous wiping means is divided into an upper portion and a lower portion and wherein there is an annular spacing around said sampling conduit and between said upper and lower portions.

5. Apparatus as defined in claim 2 wherein said solvent supply means is adapted to supply solvent when the sampling conduit is in its sample-intake position and wherein said air-moving means is adapted to operate when the sampling conduit is in its sample-discharge position.

6. Apparatus for washing a sampling conduit comprising
    (a) a housing in relation to which said sampling conduit moves up and down, said housing comprising porous wiping means in snug contact with said needle;
    (b) means to distribute a supply of wash liquid to said needle through said porous wiping means;
    (c) means to move air through said porous wiping means at a position below said wash-liquid supply means; and
    (d) means to remove said air from said washing means at a position below said wash-liquid supply means.

7. Apparatus as defined in claim 6 wherein said porous wiping means is a sintered material having a pore size of from about 20 to 40 microns.

8. Apparatus as defined in claim 6 wherein said porous wiping means is divided into an upper portion and a lower portion and wherein there is an annular spacing around said sampling conduit and between said upper and lower portion.

9. Apparatus as defined in claim 6 wherein said solvent supply means is adapted to supply solvent when the sampling conduit is in its sample-intake position and wherein said air-moving means is adapted to operate when the sampling conduit is in its sample-discharge position.

10. Apparatus as defined in claim 2 wherein a fluid seal is maintained between said sampling conduit and the walls of said vertical channel at a position above and at a position below said outlet port, each said seal comprising a sleeve of compressible resin forming part of the walls of said channel, and stress rings mounted above and below said sleeves, said stress rings forming means to displace the upper and lower extremities of said sleeves inwardly to form a sealing contact with said sample-intake conduit, and means to compress said stress rings into said sleeves.

11. Apparatus as defined in claim 2 wherein said sleeves are formed of an organic resin reinforced polyfluorocarbon resin.

12. Apparatus as defined in claim 2 wherein said stress rings comprise a wedge shaped protrusion adapted to push into the sleeve against which it is compressed.

13. In a process for injecting a liquid into apparatus of the type comprising a sample loop, means to supply discrete samples to said loop at a first end thereof and means to supply solvent from the second end thereof to push said sample out of said injection apparatus at an injector outlet port, and wherein said apparatus also comprises means to continuously supply solvent through a conduit by-passing said sample loop and thence to a said injector outlet port at the same site at which said sample loop is emptied into said outlet port, the improvement comprising the steps of
   (a) supplying discrete samples to said loop via a sampling conduit having an outlet orifice and that forms part of said sample loop and is moveable in a vertical channel between a sample-intake position and a sample-discharge position;
   (b) discharging sample from said sampling conduit through said orifice into said outlet port; and
   (c) utilizing a portion of a plug member carried by said conduit below said orifice for sealing said channel below said outlet port, when said sampling conduit is in the raised position,
   (d) said means to continuously supply solvent including an annular passage proximate to said orifice when said sampling conduit is in its sample-discharge position.

14. A process for washing a liquid sampling conduit comprising the steps of
   (a) maintaining the liquid-wetted exterior of said conduit in snug contact with a relatively soft porous mass;
   (b) reciprocating said conduit in relation to said mass;
   (c) supplying a cleaning liquid to said surface through one portion of said mass; and
   (d) pulling air through a second and lower portion of said mass; said air preventing leakage of any solvent from said porous mass.

* * * * *